United States Patent
Liu et al.

(10) Patent No.: US 11,007,176 B2
(45) Date of Patent: May 18, 2021

(54) USE OF ACTIN DEPOLYMERIZING AGENTS FOR THE TREATMENT OF ANXIETY DISORDERS

(71) Applicant: TZU CHI UNIVERSITY, Hualien (TW)

(72) Inventors: Ingrid Yichun Liu, Hualien (TW); Hsien-Ting Huang, Hualien (TW); Chia-Sheng Pai, Hualien (TW)

(73) Assignee: TZU CHI UNIVERSITY, Hualien (TW)

( * ) Notice: Subject to any disclaimer, the term of this patent is extended or adjusted under 35 U.S.C. 154(b) by 0 days.

(21) Appl. No.: 16/279,366

(22) Filed: Feb. 19, 2019

(65) Prior Publication Data

US 2020/0261412 A1     Aug. 20, 2020

(51) Int. Cl.
| | | |
|---|---|---|
| A61K 31/403 | (2006.01) | |
| A61K 31/5513 | (2006.01) | |
| A61P 25/22 | (2006.01) | |
| A61K 31/5517 | (2006.01) | |
| A61K 38/17 | (2006.01) | |

(52) U.S. Cl.
CPC ........ *A61K 31/403* (2013.01); *A61K 31/5513* (2013.01); *A61K 31/5517* (2013.01); *A61K 38/1709* (2013.01); *A61P 25/22* (2018.01)

(58) Field of Classification Search
CPC .............. A61K 31/403; A61K 31/5513; A61K 31/5517; A61K 38/1709; A61P 25/22
See application file for complete search history.

(56) References Cited

FOREIGN PATENT DOCUMENTS

| | | |
|---|---|---|
| CN | 1568974 A | 1/2005 |
| CN | 101416962 A | 4/2009 |
| CN | 103816149 A | 5/2014 |
| KR | 20130048354 A | 5/2013 |
| KR | 20180022416 A | 3/2018 |
| WO | 90/13293 A1 | 11/1990 |

OTHER PUBLICATIONS

Lamprecht, "The roles of the actin cytoskeleton in fear memory formation", Frontiers in Behavioral Neuroscience, vol. 5, Article 39, pp. 1-10, Jul. 2011, 10 pages total.
Zhang et al., "Treatment with gelsolin reduces brain inflammation and apoptotic signaling in mice following thermal injury", Journal of Neuroinflammation, vol. 8, No. 118, pp. 1-18, 2011, 18 pages total.
Search Report, dated Dec. 13, 2019, issued by the Taiwanese Intellectual Property Office in Taiwanese Patent Application No. 108105491.
Ackermann et al. "Activity-induced targeting of profilin and stabilization of dendritic spine morphology," Nature Neuroscience, Nov. 2003, vol. 6, No. 11, pp. 1194-1200 (total 7 pages).
Ahlgren, H. et al., "The Nuclear Calcium Signaling Target, Activating Transcription Factor 3 (ATF3), Protects against Dendrotoxicity and Facilitates the Recovery of Synaptic Transmission after an Excitotoxic Insult," The Journal of Biological Chemistry, Apr. 4, 2014, vol. 289, No. 14, pp. 9970-9982 (total 14 pages).
Alvarez, R. P. et al., "Contextual Fear Conditioning in Humans: Cortical-Hippocampal and Amygdala Contributions," The Journal of Neuroscience, Jun. 11, 2008, vol. 28, pp. 6211-6219 (total 9 pages).
Brooks, A. et al., "Endoplasmic reticulum stress-dependent activation of ATF3 mediates the late phase of ischemic preconditioning," Journal of Molecular and Cellular Cardiology, 2014, vol. 76, pp. 138-147 (total 10 pages).
Campbell G. et al., "Upregulation of activating transcription factor 3 (ATF3) by intrinsic CNS neurons regenerating axons into peripheral nerve grafts," Experimental Neurology, 2005, vol. 192, pp. 340-347 (total 8 pages).
Chen BP. et al., "Analysis of ATF3, a Transcription Factor Induced by Physiological Stresses and Modulated by gadd153/Chop10," Molecular and Cellular Biology, Mar. 1996, vol. 16, No. 3, pp. 1157-1168 (total 15 pages).
Chun Zhang et al., "Transcriptional activation of the human stress-inducible transcriptional repressor ATF3 gene promoter by p53," Biochemical and Biophysical Research Communications, 2002, vol. 297, pp. 1302-1310 (total 9 pages).
Critchley et al., "Fear Conditioning in Humans: The Influence of Awareness and Autonomic Arousal on Functional Neuroanatomy," Neuron, Feb. 14, 2002, vol. 33, pp. 653-663 (total 11 pages).
Francis JS. Et al., "Over expression of ATF-3 protects rat hippocampal neurons from in vivo injection of kainic acid," Molecular Brain Research, 2004, vol. 124, pp. 199-203 (total 5 pages).
Giachero, M. et al., "Hippocampal structural plasticity accompanies the resulting contextual fear memory following stress and fear conditioning," Learning & memory (Cold Spring Harbor, N.Y.), 2015, vol. 20, pp. 611-616 (total 7 pages).
Gilchrist, M. et bal., "Activating transcription factor 3 is a negative regulator of allergic pulmonary inflammation," The Journal of Experimental Medicine, Sep. 15, 2008, vol. 205, No. 10, pp. 2349-2357 (total 9 pages).
Moore, D.L. et al., "Multiple Transcription Factor Families Regulate Axon Growth and Regeneration," Developmental Neurobiology, 2011, vol. 71, pp. 1186-1211 (total 26 pages).
Hai et al., "The molecular biology and nomenclature of the activating transcription factor/cAMP responsive element binding family of transcription factors: activating transcription factor proteins and homeostasis," Gene, 2001, vol. 273, pp. 1-11 (total 11 pages).
Hai. et al., "ATF3 and Stress Responses," Gene Expression, 1999, vol. 7, pp. 321-335 (total 15 pages).

(Continued)

*Primary Examiner* — Robert C Hayes
(74) *Attorney, Agent, or Firm* — Sughrue Mion, PLLC (57) ABSTRACT

The present invention relates to a novel use of actin depolymerizing agents, particularly cytochalasins or derivatives thereof for inhibiting or reversing actin polymerization. Therefore, the present invention provides a method for preventing or treating anxiety disorders and/or alleviating the symptoms thereof, comprising administering to a subject in need thereof a therapeutically effective amount of an actin depolymerizing agent or a derivative thereof.

7 Claims, 6 Drawing Sheets

Specification includes a Sequence Listing.

(56) References Cited

OTHER PUBLICATIONS

Hai et al., "Cross-family dimerization of transcription factors Fos/Jun and ATF/CREB alters DNA binding specificity," Proceedings of National Academy Sciences of the United States America, May 1, 1991, vol. 88, No. 9, pp. 3720-3724 (total 6 pages).
Harper et al., "Wounding activates p38 map kinase and activation transcription factor 3 in leading keratinocytes," Journal of Cell Sciences, 2005, vol. 118, No. 15, pp. 3471-3485 (total 15 pages).
Hartman et al., "Role for Activating Transcription Factor 3 in Stress-Induced β-Cell Apoptosis," Molecular and Cellular Biology, Jul. 2004, vol. 24, No. 13, pp. 5721-5732 (total 12 pages).
Heinrichs et al., "Dendritic structural plasticity in the basolateral amygdala after fear conditioning and its extinction in mice," Behavioural Brain Research, 2013, vol. 248, pp. 80-84 (total 5 pages).
Hlushchenko et al., "Dendritic Spine Actin Dynamics in Neuronal Maturation and Synaptic Plasticity," Cytoskeleton, 2016, pp. 1-7 (total 7 pages).
Hotulainen et al., "Defining mechanisms of actin polymerization and depolymerization during dendritic spine morphogenesis," The Journal of Cell Biology, Apr. 20, 2009, vol. 185, No. 2, pp. 323-339 (total 17 pages).
Hotulainen et al., "Actin in dendritic spines: connecting dynamics to function," The Journal of cell biology, May 17, 2010, vol. 189, No. 4, pp. 619-629 (total 12 pages).
Hunt D, H.-I. K., Mason MR, Coffin RS, Lieberman AR, Winterbottom J, Anderson PN. (2004). "ATF3 upregulation in glia during Wallerian degeneration: differential expression in peripheral nerves and CNS white matter." BMC Neurosci. 5(9), pp. 1-12.
Hunt, D., Raivich, G. & Anderson, P. N. (2012). "Activating transcription factor 3 and the nervous system." Frontiers in molecular neuroscience 5(7), pp. 1-17.
Isacsson A, K. M., Dahlin LB (2005). "Induction of activating transcription factor 3 (ATF3) by peripheral nerve compression." Scand J Plast Reconstr Surg Hand Surg. 39: 65-72.
Izquierdo, I., Furini, C. R. & Myskiw, J. C (2016). "Fear Memory." Physiological reviews 96: 695-750.
Kehat, I., Hasin, T. & Aronheim, A. (2006). "The role of basic leucine zipper protein-mediated transcription in physiological and pathological myocardial hypertrophy." Annals of the New York Academy of Sciences 1080: 97-109.
Keifer, O. P., Jr. et al. (2015). "Voxel-based morphometry predicts shifts in dendritic spine density and morphology with auditory fear conditioning." Nature communications 6: 8582, pp. 1-12.
Khaitlina, S., Fitz, H. & Hinssen, H. (2013). "The interaction of gelsolin with tropomyosin modulates actin dynamics." The FEBS journal 280: 4600-4611, pp. 1-12.
Kim, J., Hwang JY, Lee DY, Song EH, Park KJ, Kim GH, Jeong EA, Lee YJ, Go MJ, Kim DJ, Lee SS, Kim BJ, Song J, Roh GS, Gao B, Kim WH. (2014). "Chronic ethanol consumption inhibits glucokinase transcriptional activity by Atf3 and triggers metabolic syndrome in Vivo." J Biol Chem 289(39): pp. 27065-27079 (total 16 pages).
Lamprecht, R., Farb, C. R., Rodrigues, S. M. & LeDoux, J. (2006). "Fear conditioning drives profilin into amygdala dendritic spines." Nature Neuroscience, Apr. 2006, vol. 9, No. 4, pp. 481-483 (total 3 pages).
Lee, Y. S. et al., (2013), "Hypothalamic ATF3 is involved in regulating glucose and energy metabolism in mice." Diabetologia 56: pp. 1383-1393 (total 11 pages).
Leonardo Restivo, G. V., Bruno Bontempi, and Martine Ammassari-Teule (2009). "The Formation of Recent and Remote Memory Is Associated with Time-Dependent Formation of Dendritic Spines in the Hippocampus and Anterior Cingulate Cortex." The Journal of Neuroscience 29(25): pp. 8206-8214 (total 9 pages).
Leuner, B. S., T. (2012). "Stress, anxiety, and dendritic spines: What are the connections?" J. Neuroscience 251: 108-119, pp. 1-12.
Li HF, C. C., Liao WJ, Lin H, Yang RB. (2010). "ATF3-mediated epigenetic regulation protects against acute kidney injury." J Am Soc Nephrol 21: 2010, pp. 1003-1013 (total 11 pages).
Mantzur, L., Joels, G. & Lamprecht, R. (2009). "Actin polymerization in lateral amygdala is essential for fear memory formation." Neurobiology of Learning and Memory 91: 85-88.
Maroun, M. e. a. (2013). "Fear extinction deficits following acute stress associate with increased spine density and dendritic retraction in basolateral amygdala neurons." The European journal of neuroscience 38: 2611-2620 (total 19 pages).
Matus, A. (2000). "Actin-Based Plasticity in Dendritic Spines." Science, Oct. 27, 2000, vol. 290: pp. 754-758 (total 6 pages).
Middei, S. e. a. (2012). "CREB selectively controls learning-induced structural remodeling of neurons." Learning & memory (Cold Spring Harbor, N.Y.) 19, pp. 330-336 (total 8 pages).
Moczulska, K. E. et al., (2013). "Dynamics of dendritic spines in the mouse auditory cortex during memory formation and memory recall." Proceedings of the National Academy of Sciences of the United States of America, Nov. 5, 2013, vol. 110, No. 45: pp. 18315-18320 (total 6 pages).
Neuhoff, H. et al., (2005). "The actin-binding protein profilin I is localized at synaptic sites in an activity-regulated manner." European Journal of Neuroscience, vol. 21: pp. 15-25 (total 11 pages).
Ni-Chun Chung, Y.-H. H., Chuan-Hsiung Chang, James C. Liao, Chih-Hsien Yang, Chien-Chang Chen, Ingrid Y. Liu (2015). "Behavior Training Reverses Asymmetry in Hippocampal Transcriptome of the $Ca_v3.2$ Knockout Mice." PLoS One 10(3): e0118832, pp. 1-16.
Nie, D. et al., (2015). "The Stress-Induced Atf3-Gelsolin Cascade Underlies Dendritic Spine Deficits in Neuronal Models of Tuberous Sclerosis Complex." The Journal of neuroscience: the official journal of the Society for Neuroscience 35(30): pp. 10762-10772 (total 11 pages).
Niesmann, K. et al., (2011). "Dendritic spine formation and synaptic function require neurobeachin." Nature communications 2: 557, pp. 1-10.
Nils Z. Borgesius, M. C. d. W., Ingrid van der Pluijm, Azar Omrani, Gerben C. M. Zondag, Gijsbertus T. J. van der Horst, David W. Melton, Jan H. J. Hoeijmakers, Dick Jaarsma, and Ype Elgersma. (2011). "Accelerated Age-Related Cognitive Decline and Neurodegeneration, Caused by Deficient DNA Repair," The Journal of Neuroscience, Aug. 31, 2011, 31(35): pp. 12543-12553 (total 11 pages).
Parsons, R. G. R., K. J. (2013). "Implications of memory modulation for post-traumatic stress and fear disorders." Nature Neuroscience, vol. 16, No. 2, Feb. 2013: pp. 146-153 (total 8 pages).
Pernhorst, K., Herms S, Hoffmann P, Cichon S, Schulz H, Sander T, Schoch S, Becker AJ, Grote A. (2013). "TLR4, ATF-3 and IL8 inflammation mediator expression correlates with seizure frequency in human epileptic brain tissue." Seizure 22(8): pp. 675-678 (total 4 pages).
Rao, J., Qian X, Li G, Pan X, Zhang C, Zhang F, Zhai Y, Wang X, Lu L. Am. (2015). "ATF3-mediated NRF2/HO-1 signaling regulates TLR4 innate immune responses in mouse liver ischemia/reperfusion injury," American Journal of Transplantation, 15: 76-87, (pp. 1-12).
Sandnes, D., Müller KM, Akhtar K, Johansen EJ, Christoffersen T, Thoresen GH. (2010). "Induction of LRF-1/ATF3 by vasopressin in hepatocytes: role of MAP kinases," Cellular Physiology and Biochemistry, 25(4-5): pp. 523-532 (total 10 pages).
Sargin, D. et al., (2013). "CREB regulates spine density of lateral amygdala neurons: implications for memory allocation." Frontiers in behavioral neuroscience, Dec. 2013, vol. 7, Article 209, p. 1-9.
Serita, T., Fukushima, H. & Kida, S. (2017). "Constitutive activation of CREB in mice enhances temporal association learning and increases hippocampal CA1 neuronal spine density and complexity." Scientific reports 7(42528), pp. 1-12.
Shikha Snigdha, G. A. P., Arpine Petrosyan, Brad M. Loertscher, Andre' P. Dieskau, Larry E. Overman, and Carl W. Cotman (2016). "H3K9me3 Inhibition Improves Memory, Promotes Spine Formation, and Increases BDNF Levels in the Aged Hippocampus." The Journal of Neuroscience 36(12): pp. 3611-3622 (total 12 pages).
Song, D. Y. et al., (2008). "Axotomy-induced dopaminergic neurodegeneration is accompanied with c-Jun phosphorylation and activation transcription factor 3 expression." Experimental neurology 209: pp. 268-278.

(56) References Cited

OTHER PUBLICATIONS

St Germain C, N. N., Ma L, Garbuio K, Hai T, Dimitroulakos (2010). "Cisplatin induces cytotoxicity through the mitogen-activated protein kinase pathways and activating transcription factor 3." J. Neoplasia, vol. 12, No. 7: pp. 527-538 (total 12 pages).

Takeda M, K. H., Takamiya A, Yoshida A, Kiyama H (2000). "Injury-specific expression of activating transcription factor-3 in retinal ganglion cells and its colocalized expression with phosphorylated c-Jun." Invest Ophthalmol Vis Sci., Aug. 2000, vol. 41, No. 9: pp. 2412-2421 (total 10 pages).

Taketani, K. et al., (2012). "Key role of ATF3 in p53-dependent DR5 induction upon DNA damage of human colon cancer cells," Oncogene, 2012, 31: pp. 2210-2221 (total 23 pages).

Takumi Yoshida, H. S., Michihiro Mitobe, Ken Tsuchiya, Satsuki Shirota, Sayoko Nishimura, Shunji Shiohira, Hiroshi Ito, Kiyoshi Nobori, Steven R. Gullans, Takashi Akiba and Kosaku Nitta (2008). "ATF3 Protects against Renal Ischemia-Reperfusion Injury." JASN 19(2): pp. 217-224 (total 8 pages).

Tanaka, Y. et al., (2011). "Systems analysis of ATF3 in stress response and cancer reveals opposing effects on pro-apoptotic genes in p53 pathway." Plos one, Oct. 2011, vol. 6, Issue 10: e26848, pp. 1-12.

Tsujino H, K. E., Fukuoka T, Dai Y, Tokunaga A, Miki K, Yonenobu K, Ochi T, Noguchi K (2000). "Activating transcription factor 3 (ATF3) induction by axotomy in sensory and motoneurons: A novel neuronal marker of nerve injury." Molecular and Cellular Neuroscience. 15: pp. 170-182 (total 13 pages).

Wang, L. et al., (2012). "Increased inflammation and brain injury after transient focal cerebral ischemia in activating transcription factor 3 knockout mice," Neuroscience 220: pp. 100-108 (total 9 pages).

Wu ZY, W. Z., Sun SJ, Yuan J, Jiao SC. (2014). "Activating transcription factor 3 promotes colon cancer metastasis." Tumour Biol 35(8): 8329-8334 (total 6 pages).

Yin, X., Dewille, J. W. & Hai, T. (2008). "A potential dichotomous role of ATF3, an adaptive-response gene, in cancer development." Oncogene 27: 2118-2127 (total 10 pages).

Yuan, X. et al., (2013). "ATF3 suppresses metastasis of bladder cancer by regulating gelsolin-mediated remodeling of the actin cytoskeleton." Cancer research 73: 3625-3627 (total 15 pages).

Zhang SJ, B. B., Lau D, Hayer S, Dick O, Schwaninger M, Veltkamp R, Zou M, Weiss U, Bading H. (2011). "A signaling cascade of nuclear calcium-CREB-ATF3 activated by synaptic NMDA receptors defines a gene repression module that protects against extrasynaptic NMDA receptor-induced neuronal cell death and ischemic brain damage." The Journal of Neuroscience, Mar. 30, 2011, 31(13): pp. 4978-4990 (total 13 pages).

Trendowski, M. (2015). "Using Cytochalasins to Improve Current Chemotherapeutic Approaches" Anticancer Agents Med Chem 15(3): 327-335 (total 9 pages).

Figure 6

USE OF ACTIN DEPOLYMERIZING AGENTS FOR THE TREATMENT OF ANXIETY DISORDERS

FIELD OF THE INVENTION

The present invention relates to a novel use of actin depolymerizing agents for treating anxiety disorders.

BACKGROUND OF THE INVENTION

Fear is the most profoundly understood emotion in terms of the brain structure and neural circuits involved. Because fear memory expression plays a key role in various anxiety disorders, including post-traumatic stress disorder (PTSD), panic attacks, and phobias, understanding its molecular mechanism is essential (Parsons 2013, Izquierdo 2016).

Various paradigms have been used to study fear memory formation; the most widely used is classical fear conditioning (Izquierdo 2016). Fear conditioning is a form of associative learning, and the freeze response to conditioning contexts and cues is conserved across species, including humans (Izquierdo 2016). Excess expression of fear memory, indicated by enhanced freezing behavior in mouse models, has been considered a type of PTSD-like symptom. The brain structures involved in fear memory include the cortex, hippocampus, and amygdala (Critchley 2002, Alvarez 2008, Izquierdo 2016). Memory formation involves various cellular and molecular changes including structural alteration of dendritic spines for synaptic plasticity. Dendritic spines, a cellular-level change responsible for synaptic plasticity, are small actin-rich protrusions on the neurites (Niesmann 2011). The organization, dynamics, and density of spines are associated with the strength of synaptic transmission and indicate the efficiency of memory formation (Niesmann 2011, Moczulska 2013).

Activating transcription factor 3 (ATF3) is induced under stress conditions and is predominantly expressed in the hippocampus. Stress signals induce ATF3 through multiple pathways and in a cell type dependent manner. Cumene hydroperoxide activates JNK signal and phosphorylate ATF2 and c-Jun, which subsequently binds to the ATF3 promoter and activate its expression (Hai 1991). Cisplatin is a chemotherapy medicine that induces expression of ATF3 through the p38, ERK and JNK signaling (St Germain C 2010). When human colorectal carcinoma cells are exposed to ultraviolet (UV) or proteasome inhibitor MG132, ATF3 is upregulated via p53 signaling (Chun Zhanga 2002). Moreover, ATF3 is also induced by extracellular signals including serum, fibroblast growth factor (FGF), epidermal growth factor (EGF) and cytokines (Goldberg 2011). In animal models, ATF3 is induced in the heart by myocardial ischemia and myocardial ischemia coupled with reperfusion (ischemia-reperfusion) (Brooks 2014). In the liver, ATF3 can be activated by hepatic ischemia (Rao 2015) and partial hepatectomy (Sandnes 2010). In addition, chemicals including alcohol (Kim 2014), carbon tetrachloride (Chen B P 1996), and acetaminophen (Hai 1997, Hai T 1999) can upregulate expression of ATF3. ATF3 can also be activated in the brain by seizure (Pernhorst 2013), in the kidney by renal ischemia-reperfusion (Takumi Yoshida 2008), in the skin by wounding (Harper 2005), in the peripheral nerves by axotomy (Tsujino H 2000), and in the thymocytes by CD31 (Wu Z Y 2014). ATF3 is also expressed in injured neurons, such as the peripheral nerve (Tsujino H 2000, Isacsson A 2005), optic nerve (Takeda M 2000), post-seizure brain (Chen B P 1996, Francis J S 2004), and the CNS glia (Hunt D 2004).

Changes in the number and morphology of dendritic spines involve molecular-level mechanisms. Studies have described how the involvement of cyclic adenosine monophosphate (AMP) responsive element binding protein (CREB) transcription manipulates the morphology and number of dendritic spines (Sargin 2013, Serita 2017). CREB activation leads to enhanced hippocampal-dependent learning in trace fear conditioning and increased dendritic spine density, indicating the vital role of CREB transcription factors in dendritic spine density (Serita 2017).

ATF3 belongs to a large family of transcription factors including CREB and inducible cAMP early repressor (ICER). The ATF/CREB/ICER transcription factors contains the basic leucine zipper (bZIP) domain that often function as dimers using two extended α-helices to bind DNA and regulate gene expression (Chen B P 1996). In the hippocampal neurons, ATF3 has been proved to be a direct target of the CREB. Induction of ATF3 expression by CREB is initiated by calcium entry through synaptic NMDA receptors (Zhang S J 2011). This stress-induced transcription factor can form homodimers or heterodimers to regulate gene transcription. ATF3 homodimer is a transcription repressor, while forming a heterodimer with other proteins becomes a transcription activator (Hai T 2001). ATF3 is involved in various physiological and pathological functions, acting as a tumor suppressor or oncogenic gene in various cancers (Yin 2008, Tanaka 2011, Taketani 2012) and regulating glucagon and insulin levels (Lee 2013). It also regulates arterial dilation during cardiac development (Kehat 2006) and is associated with inflammation (Gilchrist, Henderson et al. 2008, Tanaka 2011, Hunt 2012, Wang 2012) as well as endoplasmic reticulum (ER)-induced stress responses (Hunt 2012). Furthermore, it has been reported to perform several vital roles in the nervous system, including neuronal growth (Hunt 2012), nerve cell protection (Hunt 2012, Ahlgren 2014) and neurodegeneration (Song 2008).

ATF3 is upregulated in age-related cognitive decline and neurodegeneration models caused by deficient DNA repair (Nils Z. Borgesius 2011). Previous studies also showed that ATF3 is required for neuron protection (Zhang S J 2011), neuron regenerating (Campbell G 2005) and axon growth (Lindwall C 2004). Though the role of ATF3 in stress condition is well studied, its function in fear-induced stress condition and memory formation remains unclear.

Cytochalasins are fungal metabolites that have the ability to bind to actin filaments and block polymerization and the elongation of actin. As a result of the inhibition of actin polymerization, cytochalasins can change cellular morphology, inhibit cellular processes such as cell division, and even cause cells to undergo apoptosis. Cytochalasins are microfilament-directed agents most commonly known for their use in basic research to understand cytoskeletal mechanisms. Research has shown that cytochalasins could be used to supplement current chemotherapeutic measures to improve efficacy rates, as well as decrease the prevalence of drug resistance in the clinical setting (see Anticancer Agents Med Chem. 2015 March; 15(3): 327-335).

KR 20130048354 A discloses a composition comprising cytochalasin B as an active ingredient for treating and preventing cancer disease. CN 103816149 A discloses the application of the cytochalasin H in preparation of Parkinson's disease resistant nerve-protective drugs. CN 101416962 A and CN 1568974 A disclose the use of cytochalasin D in preparing anti-tumor medicine for treating cancer, such as esophageal cancer, stomach cancer, breast cancer and liver cancer. WO 90/13293 A1 discovers that the administration of cytochalasins including cytochalasin B (CB) produces transient immunosuppression which is controllable by dose or route of administration and is reversible spontaneously or with the use of IL-2, and thus proposes a therapeutic regimen of cytochalasins to treat the undesirable hyperimmunity of transplant patients and patients with auto-immune disease and anti-tumor therapy utilizing the combination of CB and other cytochalasins, and optionally antineoplastic agents other than cytochalasins to enhance the administration of these agents with effective amounts of IL-2 or other lymphokines for reversing the immunosuppression produced during administration of cytochalasins with other antineoplastic agents. KR 20180022416 A discloses that cytochalasin D can be used as a novel skin-whitening agent. There are no prior art references disclosing the use of actin depolymerizing agents, such as cytochalasins, for treating mental disorders or alleviating the symptoms thereof.

Anxiety disorders are the most common of mental disorders and affect nearly 30 percent of adults at some point in their lives. Given the prevalence and impact of anxiety disorders, there is a need for treatments that address these issues. Therefore, the aim of the present invention is to provide a new treatment for anxiety disorders.

SUMMARY OF THE INVENTION

It is an objective of the present invention to provide methods and/or medicaments for preventing or treating anxiety disorders and/or alleviating the symptoms thereof, comprising administering to a subject in need thereof a therapeutically effective amount of an actin depolymerizing agent or a derivative thereof.

In a preferred embodiment of the invention, the anxiety disorder is post-traumatic stress disorder (PTSD), generalized anxiety disorder, social anxiety disorder, separation anxiety disorder, panic disorder, selective mutism or phobia-related disorders.

In a preferred embodiment of the invention, the phobia-related disorder is agoraphobia, social phobia, glossophobia, acrophobia, claustrophobia, aviophobia, dentophobia, hemophobia, arachnophobia, cynophobia, ophidiophobia or nyctophobia.

In a preferred embodiment of the invention, the actin depolymerizing agent is selected from cytochalasins. Cytoplasmic gelsolin can also be used as an actin depolymerizing agent.

In a preferred embodiment of the invention, the therapeutically effective amount of the actin depolymerizing agent or derivative thereof is selected from the ranges of from about 0.01 mg/kg to about 20 mg/kg, from about 0.05 mg/kg to about 15 mg/kg, from about 0.1 mg/kg to about 10 mg/kg, and from about 0.5 mg/kg to about 5 mg/kg.

In a preferred embodiment of the invention, the methods further comprise administering another anti-anxiety drug.

In a preferred embodiment of the invention, the medicaments further comprise or is for use in combination with another anti-anxiety drug.

In a more preferred embodiment of the invention, the anti-anxiety drug is selected from alprazolam (Xanax), clonazepam (Klonopin), chlordiazepoxide (Librium), diazepam (Valium), lorazepam (Ativan), and oxazepam (Serax).

In a further preferred embodiment of the invention, the method or medicament is for use in combination with psychotherapy.

The present invention is described in detail in the following sections. Other characterizations, purposes and advantages of the present invention can be easily found in the detailed descriptions and claims of the invention.

BRIEF DESCRIPTION OF THE DRAWINGS

FIG. 5 shows that loss of ATF3 increases dendritic spine density in the hippocampal region after retrieval of contextual trace fear memory. Inhibition of actin polymerization through intracranial infusion of cytochalasin D reversed the phenotype of $Atf3^{-/-}$ mice. Microscopic graphs of dendritic spines in the hippocampal CA1 region (A). Quantification of spine density of basal dendrites measured after retrieval of contextual memory for the $Atf3^{-/-}$ mice and their wild-type littermates with or without trace fear conditioning (B). mRNA expression levels of Gelsolin (C) and Profilin 1 (D) in wild-type and $Atf3^{-/-}$ mice before and after training (n=3 for each sample; W:wild type, K: knockout, N: naïve, T: trained groups, L: left hippocampus, R: right hippocampus). Position of cannula placement (AP: −2.18 mm from the bregma, DV: 1.8 mm. (E). Timeline for intracranial infusion and fear conditioning (F). Freezing percentage to context (n=4:WT saline, 4:WT treated with drug, 3: KO saline and 4: KO treated with drug) (G) and to tone (n=5:WT saline, 3: WT treated with drug, 5: KO saline and 3: KO treated with drug) (H) after injection of cytochalasin D (cytD). The results shown in the figure are plotted as mean±SE and statistically tested with one-way Anova followed by Tukey test and set a confidence level of 99% (p<0.001). a, b, and c indicate significant difference among groups with different letters (P<0.05)

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear; however, in the event of any latent ambiguity, definitions provided herein take precedence over any dictionary or extrinsic definition.

As utilized in accordance with the present disclosure, the following terms, unless otherwise indicated, shall be understood to have the following meanings.

The term "about" when used before a numerical designation, e.g., temperature, time, amount, concentration, and such other, including a range, indicates approximations which may vary by (+) or (−) 10%, 5% or 1%.

The term "comprising" or "comprises" is intended to mean that the compositions and methods include the recited elements, but not excluding others. "Consisting essentially of" when used to define medicaments and methods, shall mean excluding other elements of any essential significance to the combination for the stated purpose. Thus, a medicament or method consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "anxiety disorders" as used herein refers to a group of mental disorders characterized by significant feelings of anxiety and fear. There are several types of anxiety disorders, including, but not limited to, post-traumatic stress disorder (PTSD), generalized anxiety disorder, social anxiety disorder, separation anxiety disorder, panic disorder, selective mutism and various phobia-related disorders. The common types of phobia-related disorders include agoraphobia, social phobia, glossophobia, acrophobia, claustrophobia, aviophobia, dentophobia, hemophobia, arachnophobia, cynophobia, ophidiophobia and nyctophobia. Symptoms of anxiety disorders include, but are not limited to, excessive worrying, feeling agitated, restlessness, fatigue, difficulty in concentrating, irritability, trouble falling or staying asleep, panic attacks, avoiding social situations and irrational fears, cold, sweaty, numb or tingling hands or feet, shortness of breath, heart palpitations, dry mouth, nausea and dizziness.

The term "preventing" or "prophylaxis" as used herein refers to delaying the onset of symptoms of a susceptible subject, reducing the occurrence of a disorder or condition, or inhibiting the occurrence of the disorder or condition, or arresting the development of the disorder or condition.

The term "treating" or "treatment" as used herein denotes alleviating, relieving, reversing and/or improving a disorder or condition or one or more symptoms thereof, or stopping the symptoms of the disease or condition in a susceptible subject.

The term "subject" as used herein denotes animals, especially mammals. In one preferred embodiment, the term "subject" denotes "humans."

The term "therapeutically effective amount" as used herein refers to the amount of an active ingredient used alone or in combination with other treatments/medicaments for preventing or treating a disease or disorder. The therapeutically effective amount of an active ingredient may be higher or lower, depending on the route of administration used. For example, when direct blood administration (e.g., sublingual, pulmonary, buccal, or intranasal delivery) is used, a lower dose of the active ingredient is administered The term "pharmaceutically acceptable carrier" refers to solvents, diluents, binders, adhesives, adjuvants, excipients, acceptors, stabilizer, analogues, flavoring agents, sweetening agents, emulsifying agents or preservative agents, which are well known to persons of ordinary skill in the art, for manufacturing pharmaceutical or dietary compositions.

The term "administering" or "administration" as used herein refers to the methods that may be used to enable delivery of the composition or medicament of the present invention to the desired site of biological action. These methods include, but are not limited to, oral, intraduodenal, nasal, parenteral injection (including intravenous, subcutaneous, intramuscular, intravascular or intradermal), topical and rectal administration. In a preferred embodiment, the composition and medicament described herein are administered by parenteral injection.

The term "actin depolymerizing agent" as used herein refers to an agent that can inhibit or disrupt actin polymerization. Examples of such actin depolymerizing agents include, but are not limited to, cytochalasins and cytoplasmic gelsolin.

The term "derivative" as used herein refers to an agent that is modified from a known actin depolymerizing agent but still retains the same or has better efficacy in the inhibition of actin polymerization.

Unless otherwise required by context, singular terms shall include the plural and plural terms shall include the singular.

The present invention demonstrates that the lack of ATF3 in mice leads to increased freezing behavior in the fear-conditioning paradigm. Additionally, normal responses of the Atf3$^{-/-}$ mice to other hippocampus-dependent learning paradigms indicate that ATF3 specifically suppresses stress-induced fear memory. Along with the enhanced freezing behavior results, basal dendritic spine density in the dorsal hippocampal CA1 area of the Atf3$^{-/-}$ mice was also increased compared with their wild-type littermates. The molecular basis of this phenomenon is reflected by decreased expression of Gelsolin, a capping molecule that prevents actin polymerization and dendritic spine protrusion modulation. Hippocampal injection of cytochalasin D, an actin polymerization inhibitor, reduced the freezing behavior of the Atf3$^{-/-}$ mice to a wild-type mouse level. This indicates that normal ATF3 may suppress expression of fear memory by directly or indirectly regulating actin polymerization.

Expression of fear memory (fear response) is a highly conserved cross-species behavior, which indicates its importance to survival throughout evolution. Moderate fear memory helps organisms avoid danger and is advantageous for survival, whereas excess fear memory leads to symptoms of anxiety disorders and affects daily life (Izquierdo 2016). The present invention shows that ATF3 is a possible 'brake' to prevent overexpression of fear memory. Lacking ATF3 gene may lead to enhanced fear response observed in patients affected with anxiety disorders including PTSD.

Previous studies have reported the importance of dendritic spines under stress conditions, associative learning, and memory formation (Niesmann 2011, Leuner 2013, Moczulska 2013, Sargin 2013) and have reported that dendritic spine density increases after different fear-conditioning paradigms (Giachero 2013, Heinrichs 2013, Maroun 2013, Keifer 2015). Additionally, studies have determined the importance of CREB transcription factors in regulating dendritic morphology during learning (Middei 2012, Sargin 2013, Serita 2017). A recent study reported that constitutive CREB activation is involved in both short-term and long-term memory formation (Serita 2017). Another study determined that inactivation of CREB not only results in dendritic spine collapse but also affects downstream molecules such as α-amino-3-hydroxy-5-methyl-4-isoxazolepropionic acid receptor translocation and actin-binding proteins (Middei 2012). Apart from its role in neuronal plasticity, CREB also plays a role in activating other genes involved in neurogenesis and neuroprotection. A study reported that because ATF3 is a direct target of CREB, it is activated by CREB to protect neurons from death induced by the stimulation of extrasynaptic N-methyl-D-aspartate receptors (Zhang S J 2011). Another study suggested that ATF3 acts as a transcriptional repressor and is involved in microtubule stabilization (Ahlgren 2014). These previous studies support the finding of the present invention that actin polymerization and dendritic spine changes in the Atf3 knockouts are important in moderating the expression of fear memory.

Actin polymerization and depolymerization are vital to dendritic spine morphogenesis and dynamics (Matus 2000, Hotulainen 2009, Mantzur 2009). Gelsolin is an actin-modulating/severing protein that promotes nucleation in actin polymerization by binding to the barbed end of actin filaments and preventing its progression (Khaitlina 2013); this means that the protein is crucial to dendritic spine remodeling in synaptic plasticity (Hlushchenko 2016). Moreover, ATF3 has been determined to bind to the regulatory regions of Gelsolin, resulting in the up-regulation of Gelsolin to prevent cancer cell metastasis (Yuan 2013). Another study reported that stress-induced ATF3-Gelsolin cascade is responsible for spine deficits in the tuberous sclerosis complex (Nie 2015). Knocking down ATF3 expression with shRNA decreased Gelsolin expression and increased dendritic spine density in neuronal models of tuberous sclerosis complex. This relationship between ATF3-Gelsolin cascade and spine dynamics under stress conditions inspired us to examine the mRNA expression of Gelsolin in Atf3$^{-/-}$ mice after training. Consistent with previous report (Nie 2015), the inventors found that the expression of Gelsolin was downregulated and dendritic spine density was increased in Atf3$^{-/-}$ mice compared with their wild-type littermates. These results suggest that loss of ATF3 causes reduced expression of Gelsolin and hence a disruption in Gelsolin activity, leading to a higher dendritic spine density. The present invention is the first finding of ATF3-Gelsolin relationship in vivo.

Profilin, another class of actin-binding proteins, promotes actin polymerization at the barbed end by changing the actin nucleotide from adenosine diphosphate to adenosine triphosphate (Ackermann 2003, Lamprecht 2006, Hotulainen 2010). Profilin 1 is expressed at both presynaptic and postsynaptic sites in neurons and plays a role in dendritic spine dynamics (Neuhoff 2005), whereas Profilin 2 is highly expressed in the brain. Both the actin-capping proteins and the proteins promoting polymerization work to maintain dendritic spines only in the required regions (Hotulainen 2010). Because Profilin 1 has a function opposing that of Gelsolin, the inventors measured its expression and determined that it was down-regulated in the naïve mice group. It was found that Profilin 1expression is not related with enhanced freezing responses nor increase of dendritic spine density. Since Profilin 1 has no ATF3 binding site, other factors may be involved in promoting Profilin 1 expression and actin polymerization. Further studies are required to identify the factors involved in modifying the expression of Profilin 1 and 2, and how they interact with ATF3, maintain actin polymerization dynamics and affect the balance of fear memory expression.

Figure 6:
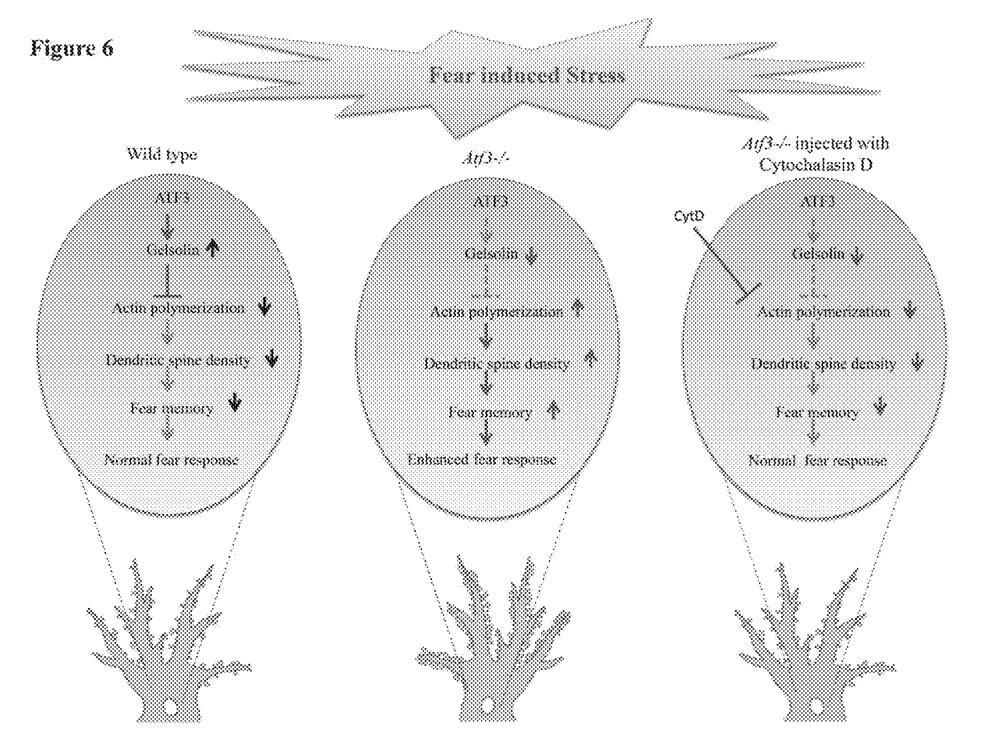
FIG. 6 shows a hypothesized mechanism for ATF3 modulation of the fear response through actin polymerization and dendritic spine reorganization. Left: ATF3 modulates normal fear response by increasing the expression of Gelsolin, which is an actin polymerization inhibitor. The increase in Gelsolin results in decreased actin polymerization and thereby decreases dendritic spine density, resulting in normal fear memory formation. Center: In the absence of ATF3, actin polymerization increases because of reduced Gelsolin expression, thereby resulting in increased spine density and higher fear response. Right: Injection of cytochalasin D, an inhibitor of actin polymerization, decreases dendritic spine density and reverses the higher freezing response of the Atf3$^{-/-}$ to the normal level.

The present invention shows that the ATF3-Gelsolin pathway controls the synaptic transmission of fear memory possibly through actin polymerization and maintains fear responses at an optimal level to prevent anxiety disorders (FIG. 6). Given the role of ATF3 as a transcription factor, it regulates many genes directly, and affects many others indirectly throughout development. Other pathways regulated by ATF3 are not excluded for their effect on expression of fear memory, but only ATF3-Gelsolin association was investigated in this invention.

In view of the above, the aim of the present invention is to provide a method or medicament for preventing or treating anxiety disorders and/or alleviating the symptoms thereof, comprising administering to a subject in need thereof a therapeutically effective amount of an actin depolymerizing agent or a derivative thereof.

The present invention further provides a use of an actin depolymerizing agent or a derivative thereof in the manufacture of a medicament for preventing or treating anxiety disorders and/or alleviating the symptoms thereof.

In the practice of the methods of the invention, a composition comprising a therapeutically effective amount of at least one type of actin depolymerizing agent is administered to a subject, e.g., a human subject, in need of the treatment. In some embodiments, the actin depolymerizing agent is selected from cytochalasins and cytoplasmic gelsolin, preferably cytochalasin D and cytoplasmic gelsolin.

The route of administration of the medicament for preventing or treating anxiety disorders and/or alleviating the symptoms thereof according to the present invention may be either oral or parenteral. The dosage form is selected appropriately according to the route of administration. Examples thereof include parenteral solutions, infusion solutions, powders, granules, tablets, capsules, pills, enteric-coated preparations, troches, liquids for internal use, suspensions, emulsions, syrups, liquids for external use, poultices, nose drops, ear drops, eye drops, inhalants, ointments, lotions, suppositories, and enteral nutrients. These can be used either alone or in combination depending on the condition of a disease. To prepare these dosage forms, auxiliary substances commonly used in the field of pharmaceutical manufacturing technology, such as pharmaceutically acceptable carriers, excipients, binders, antiseptics, antioxidants, disintegrators, lubricants, and flavoring agents, can be used as necessary.

The dose of the actin depolymerizing agent or derivative thereof for preventing or treating anxiety disorders and/or alleviating the symptoms thereof according to the present invention varies depending on the purpose of administration or the individual to whom it is to be administered (gender, age, body weight, etc.). It is contemplated that the therapeutically effective amount of the actin depolymerizing agent or derivative thereof is from the ranges of from about 0.01 mg/kg to about 20 mg/kg, preferably from about 0.05 mg/kg to about 15 mg/kg, more preferably from about 0.1 mg/kg to about 10 mg/kg, and most preferably from about 0.5 mg/kg to about 5 mg/kg in the case of parenteral administration.

In some embodiments of the invention, the anxiety disorder is post-traumatic stress disorder (PTSD), generalized anxiety disorder, social anxiety disorder, separation anxiety disorder, panic disorder, selective mutism or phobia-related disorders, preferably PTSD.

In another preferred embodiment of the invention, the phobia-related disorder is agoraphobia, social phobia, glossophobia, acrophobia, claustrophobia, aviophobia, dentophobia, hemophobia, arachnophobia, cynophobia, ophidiophobia or nyctophobia.

In some embodiments of the invention, the method further comprises administering another anti-anxiety drug.

In some embodiments of the invention, the medicament further comprises or is for use in combination with another anti-anxiety drug.

The method or medicament of the invention can be used alone or in combination with other treatments. In one preferred embodiment, the method or medicament is for use in combination with another anti-anxiety drug. In another preferred embodiment, the method or medicament is for use in combination with psychotherapy. In a further preferred embodiment, the composition used in the method or the medicament is administered simultaneously or separately with one or more therapeutic agents for preventing or treating anxiety disorders and/or alleviating the symptoms thereof.

In a preferred embodiment of the invention, the anti-anxiety drug is selected from alprazolam (Xanax), clonazepam (Klonopin), chlordiazepoxide (Librium), diazepam (Valium), lorazepam (Ativan) and oxazepam (Serax).

Having now generally described the invention, the same may be more readily understood through reference to the following examples, which provide exemplary protocols for testing the effect of actin depolymerizing agent in the treatment of anxiety disorders. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLES

The data presented in the following examples were calculated and plotted using the mean as a central tendency with standard error. Two-way analysis of variation followed by Holm-Sidak test was used for all Pairwise Multiple Comparison Procedures (behavioral results for DFC and TFC). One-way analysis of variation followed by Tukey's test was applied to results of radial arm maze (RAM) and contextual/tone tests after cytochalasin injection. Student's t-test was used to compare results between two groups (results of dendritic spine density). The statistical tests and results were conducted at the 95% confidence level ($p<0.05$) and 99% confidence level ($p<0.01$), to ensure the changes were significant. SPSS (IBM, New York, N.Y., USA) and GraphPad Prism (GraphPad Software, Inc., La Jolla, Calif., USA) were used for statistical analysis and to plot the charts, respectively.

Example 1: Preparation of Atf3$^{+/-}$ and Atf3$^{-/-}$ Mice

C57BL/6J wild-type male mice, originally provided by the National Laboratory Animal Center, Taiwan, were purchased and maintained undisturbed in the Lab Animal Center at Tzu Chi University, Taiwan, until the behavioral tasks were performed. The Atf3$^{+/-}$ (Atf3 heterozygous knockout) and Atf3$^{-/-}$ mice (Atf3 homozygous knockout), originally generated by T. Hai (Hartman 2004) and provided by Dr. Hen Lin at Taipei Medical University, Taiwan, were used in the experiment. The Atf3$^{-/-}$ mice were generated in the 129SVJ background, which contained the clone of ATF3 gene, and the exon B of the Atf3 was replaced with Neomycin by direct targeting. Three primers were used in PCR for genotyping and differentiating knockout allele from wild-type allele: 5'-AGAGCTTCAGCAATGGTTTGC-3' (primer 1; SEQ ID NO: 1), 5'-TGAAGAAGGTAAACACACCGTG-3' (primer 2; SEQ ID NO: 2), and 5'-ATCAGCAGCCTCTGTTCCAC-3' (primer 3; SEQ ID NO: 3). The Atf3$^{-/-}$ mice were congenic in the background of C57BL/6 for 10 generations (Hartman 2004, Li H F 2010).

All mice used for the experiments were between 12 and 14 weeks old. The animals were housed in individual plastic and metal cages with ad libitum access to food and water under a constant 12-h light/dark cycle. All the experiments on mice and behavioral analyses were double-blinded.

Example 2: Characterization of Atf3$^{+/-}$ and Atf3$^{-/-}$ Mice

To characterize the Atf3$^{+/-}$ and Atf3$^{-/-}$ mice and exclude significant deficits in development and sensory functions that might have affected their behavioral performance, the morphology, body weight, locomotor activity during the daytime and night time, and nociception functions of the wildtype, Atf3$^{+/-}$ and Atf3$^{-/-}$ mice's were investigated.

Locomotor Activity Test

Mice (daytime locomotor activity, WT: n=9; Atf3$^{+/-}$: n=10; Atf3$^{-/-}$: n=10; nighttime locomotor activity, WT: n=9; Atf3$^{+/-}$: n=9; Atf3$^{-/-}$: n=9) were placed in an open square chamber (50×50×50 cm) for 2 h with no cues or stimuli and were allowed to move freely in the chamber. A video camera and tracking system (TrackMot, Diagnostic & Research Instruments Co., Ltd., Taiwan) were used to measure their moving time and distance.

Sensory Function Tests

Tail Flick Test

Mice (WT: n=7; Atf3$^{+/-}$: n=8; Atf3$^{-/-}$: n=7) were placed in a 50-mL tube and their tails were exposed to 56° C. heat. The time until tail flick was recorded.

Pin Prick Test

The experimenter was blinded to the groups of mice. Before testing, the mice (WT: n=6; Atf3$^{+/-}$: n=6; Atf3$^{-/-}$: n=8) were placed on the testing stage and handled for 15 min. Then the blunted bent gauge needle (at 900 to the syringe) as a stimulus was rubbed to the plantar area of injured hind paw from the heel to the toes in the test. The intensity of stimulus to the plantar was increased by an upward force just sufficient to initiate the withdrawal of paws, but insufficient to penetrate the skin (no scratch or bleeding after pin prick test). The occurrence of paw withdrawal in ten trials with three applications/trials with an interval of 3-4 seconds, were summed. The percentage of withdrawal response frequency was calculated by the following formula:

Percentage of response frequency=[Number of paw withdrawals/10(number of applications)]×100

Results

Figure 1:
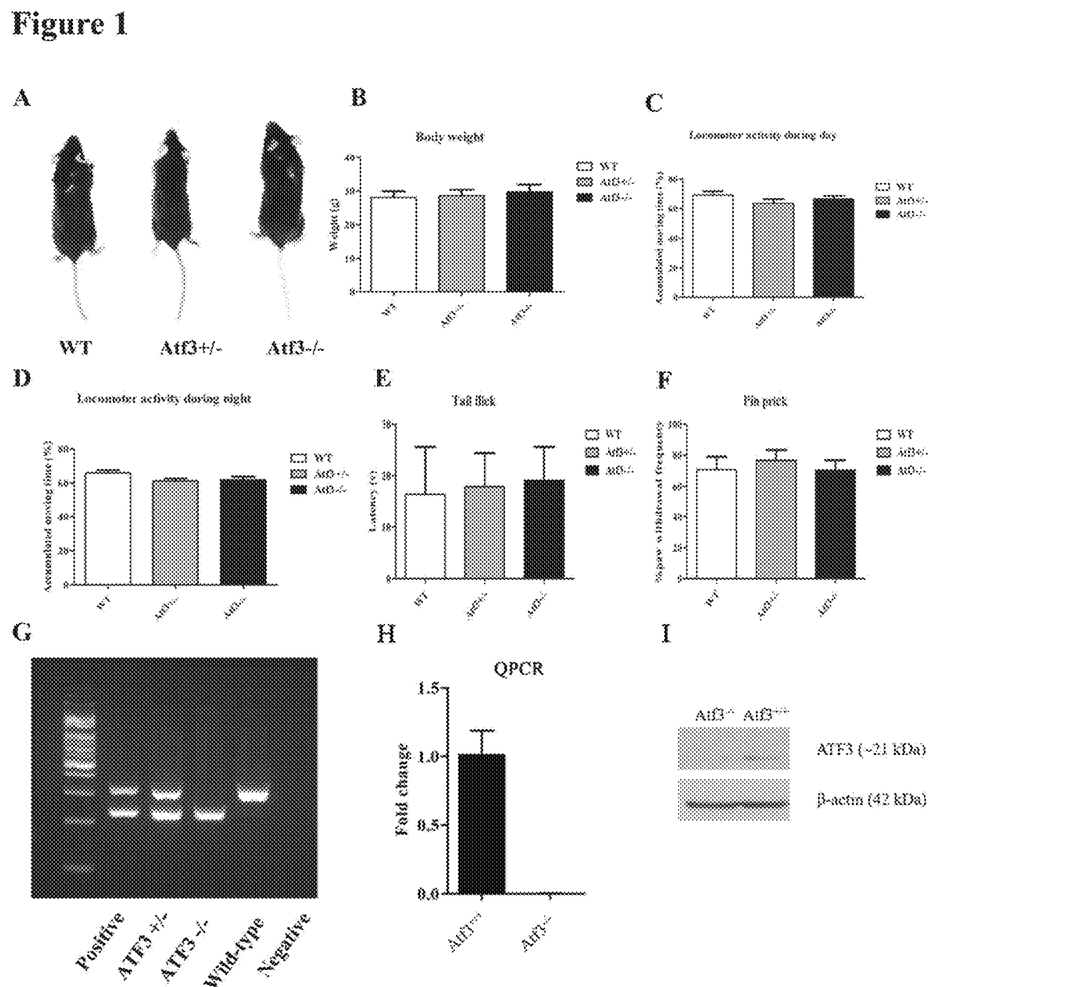
FIG. 1 shows characterization of the $Atf3^{-/-}$ mice. No significant difference (p>0.05) was recorded between $Atf3^{-/-}$ mice and their wild-type littermates in morphology (A), body weight (WT: n=7; $Atf3^{+/-}$: n=8; $Atf3^{-/-}$: n=9) (B), locomotor activity during the daytime (WT: n=9; $Atf3^{+/-}$: n=10; $Aft3^{-/-}$: n=10) (C) and nighttime (WT: n=9; $Atf3^{+/-}$: n=9; $Atf3^{-/-}$: n=9) (D), tail flick test (WT: n=7; $ATF3^{+/-}$: n=8; $Aft3^{-/-}$: n=7) (E), pin prick test (WT: n=6; $Atf3^{+/-}$: n=6; $Aft3^{-/-}$: n=8) (F). Genotyping with PCR was performed for each mouse used for behavioral experiments (G). Neither ATF3 transcript (H) nor ATF3 protein (I) was detected in the hippocampus.

As shown in FIG. 1, no significant difference (p>0.05) was recorded between Atf3$^{-/-}$ mice and their wild-type littermates in morphology (FIG. 1A), body weight (WT: n=7; Atf3$^{+/-}$: n=8; Aft3$^{-/-}$: n=9) (FIG. 1B), locomotor activity during the daytime (FIG. 1C) and nighttime (FIG. 1D), tail flick test (FIG. 1E), and pin prick test (FIG. 1F). Genotyping with PCR was performed for each mouse used for behavioral experiments (FIG. 1G). Neither ATF3 transcript (FIG. 1H) nor ATF3 protein (FIG. 1I) was detected in the hippocampus. The results indicated that Atf3$^{-/-}$ mice were grossly normal in morphology, body weight, locomotor, and nociception (tail flick and paw test) functions.

Example 3: Fear Conditioning Tests

To investigate the role of the ATF3 gene in fear memory formation, two fear-conditioning tests were performed.

Delay Fear Conditioning (DFC)

The mice were divided into three groups according to their genotype: WT (n=10), Atf3$^{+/-}$ (n=10), and Atf3$^{-/-}$ (n=11). They were placed in the conditioning chamber for 15 min per day for 3 days to allow them to adapt to the novel environment. On Day 4, the mice received three delay fear conditioning trials: a 20-s tone (6000 Hz, 85 dB; conditional stimulus [CS]) followed by a 1-s foot shock (2 mA; unconditional stimulus [US]) with an interstimulus interval of 1 min. Twenty-four hours later (Day 5), the mice were placed into the same conditioning chamber for 6 min with no tone or foot shock trial occurring for contextual testing. One hour after the contextual test, the mice were placed in a novel chamber and the tone test was performed as follows: 1 min of neither tone nor shock followed by 6 min of tone (6000 Hz, 85 dB). The fear-conditioning experiments were video recorded, and the freezing behavior (defined as no movement except for breathing) was analyzed using FreezeScan version 1.0 (Clever Sys, Inc., Reston, Va., USA). Moving range in the confined conditioning chamber was defined first and FreezeScan was used to detect the onset and completion of a freezing behavior of a mouse. Total testing time including freezing time was output as a sequential list, which indicated the occurrences of freezing behavior. The freezing percentage was calculated using the following formula:

% Freezing=(total freezing time/total test time)×100

Figure 2:
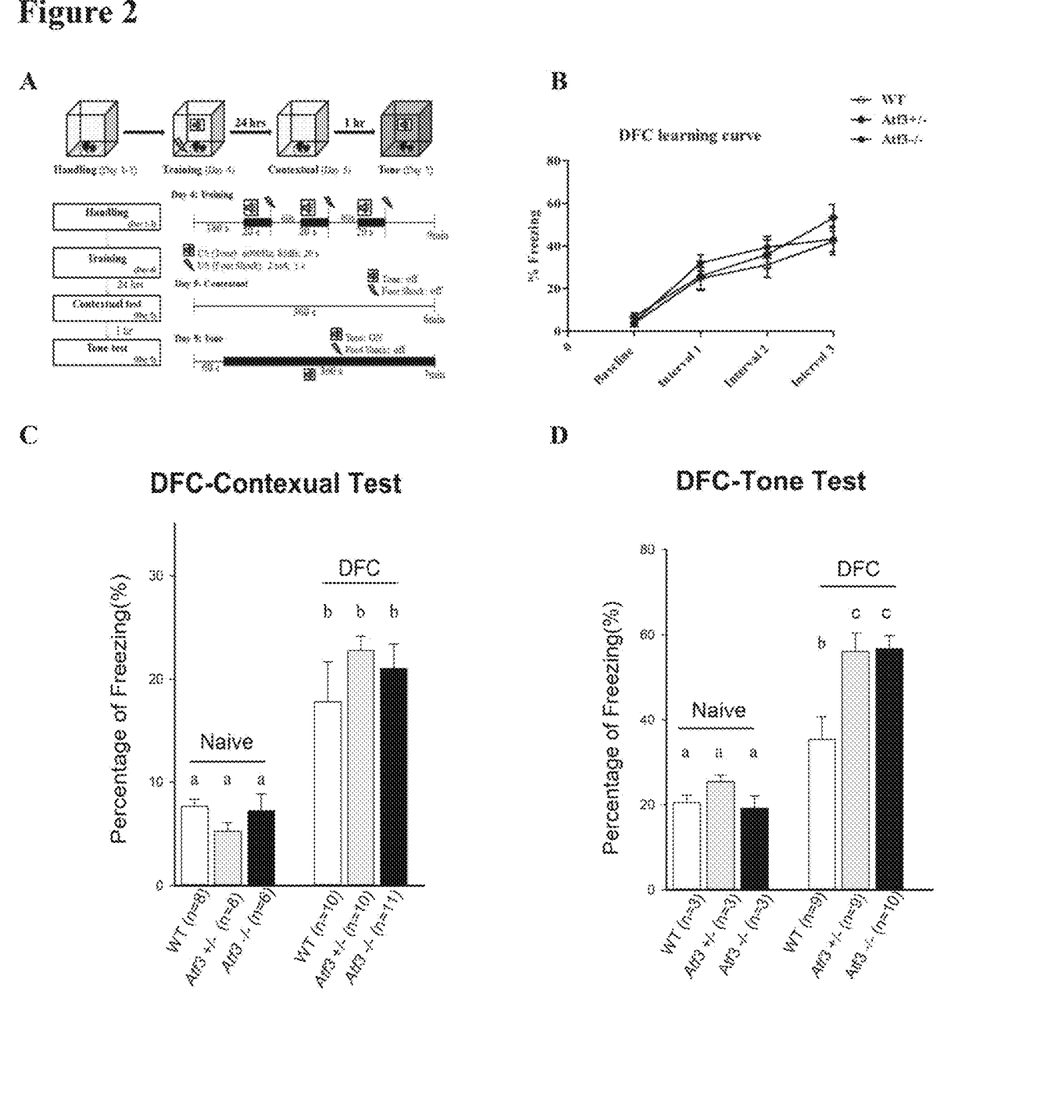
FIG. 2 shows delay fear conditioning. Mice were trained with delay fear conditioning paradigm and tested for their freezing responses to context and tone (A). Compared with their wild-type and heterozygous littermates, the $Atf3^{-/-}$ mice acquired delay fear conditioning as well (B) and retrieved contextual delay fear memory normally (WT: n=10; $Atf3^{+/-}$: n=10; $Aft3^{-/-}$: n=11) (C). However, the $Atf3^{-/-}$ mice responded to the tone cue with a significantly higher incidence of freezing behavior (WT: n=9; $Atf3^{+/-}$: n=9 $Atf3^{-/-}$: n=10) (D). a, b, and c indicate significant difference among groups with different letters (P<0.05).

The naïve fear-conditioning paradigm was performed as controls. Habituation was performed as described previously. On the training day, neither tone nor foot shock was given. Contextual and tone tests were performed as described previously. The experimental design was shown in FIG. 2A.

Results

The results of delay fear conditioning were provided in FIG. 2. Compared with their wild-type and heterozygous littermates, the Atf3$^{-/-}$ mice acquired delay fear conditioning as well (FIG. 2B) and retrieved contextual delay fear memory normally as shown in FIG. 2C (WT: n=10; Atf3$^{+/-}$: n=10; Atf3$^{-/-}$: n=11). However, the Atf3$^{-/-}$ mice responded to the tone cue with a significantly higher incidence of freezing behavior as shown in FIG. 2D (WT: n=9; Atf3$^{+/-}$: n=9 Atf3$^{-/-}$: n=10). The symbols a, b, and c indicate significant difference among groups with different letters (P<0.05).

Trace Fear Conditioning (TFC)

Figure 3:
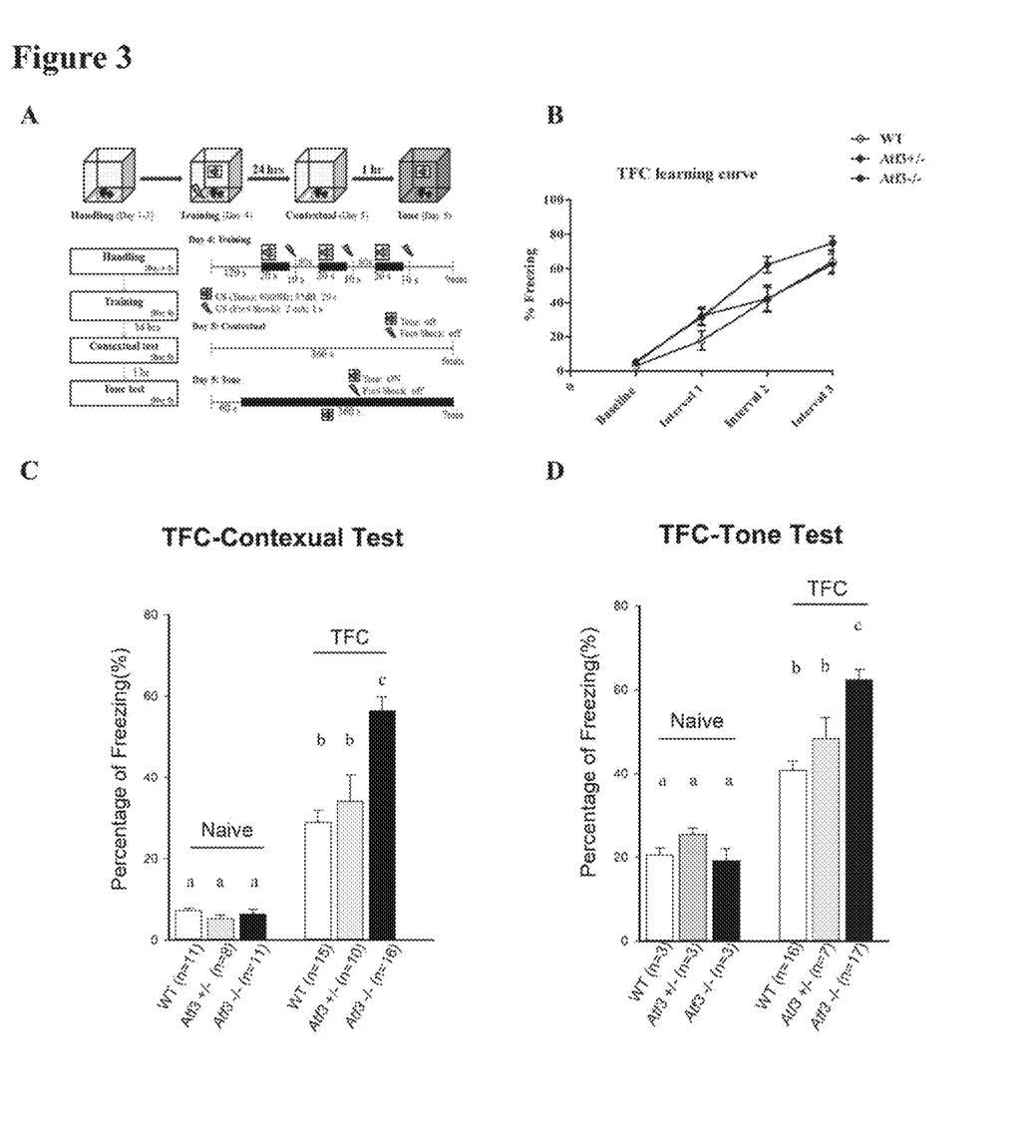
FIG. 3 shows trace fear conditioning. Mice were trained with trace fear conditioning and tested for their freezing responses to context and tone (A). The $Atf3^{-/-}$ mice acquired trace fear conditioning as well as their wild-type and heterozygous littermates (B), and responded to both contextual (C) (WT: n=15; $Atf3^{+/-}$: n=10; $Atf3^{-/-}$: n=16) and tone (D) (WT: n=16; $Atf3^{+/-}$: n=7; $Atf3^{-/-}$: n=17) cues with a significantly higher incidence of freezing behavior (p<0.05). a, b, and c indicate significant difference among groups with different letters (P<0.05).

The habituation session was performed similarly to the DFC. The mice were divided into three groups (WT: n=15; Atf3$^{+/-}$: n=10; Atf3$^{-/-}$: n=16) and placed in the conditioning chamber for 15 min per day for 3 days. On Day 4, they underwent three trace fear conditioning trials: a 20-s tone (6000 Hz, 85 dB; CS), followed by a 10-s time interval, and then a 1-s foot shock (2 mA; US). Twenty-four hours later, the mice were placed in the same conditioning chamber for 6 min with neither tone nor foot shock for contextual testing. One hour after the contextual test, the mice were placed in a novel chamber for a tone test, which was performed as follows: 1 min with neither tone nor foot shock followed by a 6-min tone (6000 Hz, 85 dB). Freezing behaviors were recorded and analyzed using the FreezeScan software, and the freezing percentage was calculated using the aforementioned formula. The experimental design was shown in FIG. 3A.

Results

The results of trace fear conditioning were provided in FIG. 3. It is noted that the Atf3$^{-/-}$ mice acquired trace fear conditioning as thoroughly as their wild-type and heterozygous littermates did (FIG. 3A), but their freeze responses to both context (FIG. 3C; WT: n=15; Atf3$^{+/-}$: n=10; Atf3$^{-/-}$: n=16) and tone (FIG. 3D; WT: n=16; Atf3$^{+/-}$: n=7; Atf3$^{-/-}$: n=17) were significantly stronger than they were among the wild-type mice (WT: n=15; Atf3$^{+/-}$: n=10; Atf3$^{-/-}$: n=16). The symbols a, b, and c indicate significant difference among groups with different letters (P<0.05).

The results of DFC and TFC indicated that the Atf3$^{-/-}$ mice exhibited enhanced freeze responses to both DFC and TFC.

Example 4: Acquisition and Retrieval of Spatial Memory

Because ATF3 is a stress-induced transcription factor and fear conditioning is a stressful training paradigm, whether the stronger memory retrieval response (freezing) of the Atf3$^{-/-}$ mice to DFC and TFC is specific to fear memory was further explored using Morris water maze test and Radial arm maze test.

Morris Water Maze Test (MWM)

Figure 4:
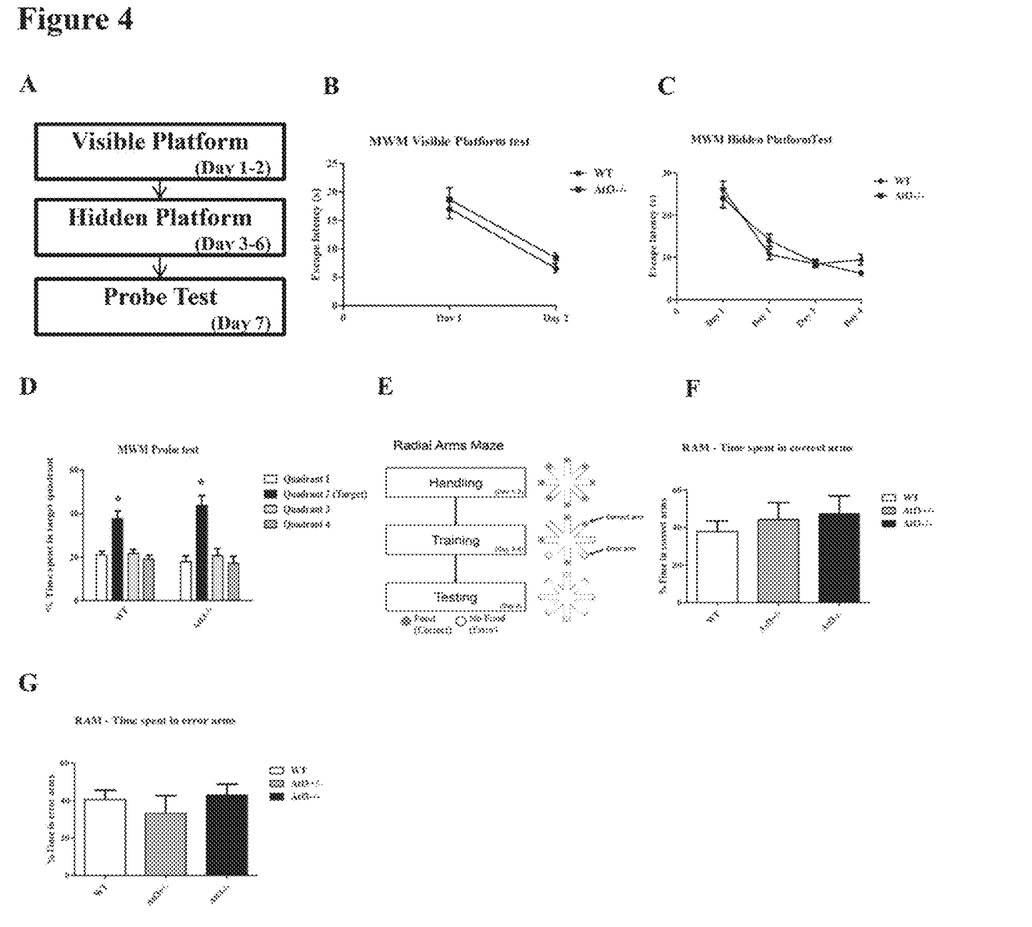
FIG. 4 shows hippocampal-dependent Morris Water maze and RAM tests. The $Atf3^{-/-}$ mice performed normally in the Morris water maze tests (A), including in visible platform (WT: n=12; $Atf3^{-/-}$: n=11) (B), hidden platform (C), and probe trial (D) tests. They also performed normally in the radial arm maze (RAM) test (WT: n=6; $Atf3^{+/-}$: n=10; $Atf3^{-/-}$: n=7) (E). No significant difference was recorded for time spent in either the correct arms (F) or the error arms (G).

A circular pool (diameter: 109 cm, platform height: 21 cm) was filled with water at room temperature (21° C.±1° C.). The water was made opaque using a nontoxic white paint (catalogue No. 187203, Palmer Paint Products, MI, USA). Four points equally dividing the pool into four quadrants were chosen, and a round platform (diameter: 10 cm) was placed in the second quadrant. A visible platform test was performed for the first 2 days (8 trials per day). One centimeter of the platform was above water level, and the mice (WT: n=12; Atf3$^{-/-}$: n=11) were trained to locate the platform within 60 seconds on the basis of different cues. The starting point for each trial was randomly selected from among the four quadrants. In the hidden platform test, the platform was placed 1 cm below water level. Every day for 4 consecutive days, each mouse underwent eight trials of 1 min each to locate the hidden platform. If they did not locate the platform, they were guided to it and left there for 10 seconds so that they could learn its location. A video camera and tracking system (TrackMot) were used to measure the escape latency. On Day 7, a probe test was performed. The platform was removed from the pool and each mouse was allowed to swim freely for 60 seconds. The percentage of time spent in each quadrant was calculated. The experimental design was shown in FIG. 4A.

Radial Arm Maze Test (RAM)

An octagonal maze was used (diameter: 20 cm; arm dimensions: 35×5×10 cm), with 0.2 g of peanut butter (Skippy Peanut Butter, MN, USA) placed at the end of each arm. Three days of habituation sessions were performed. Mice (WT: n=6; Atf3$^{+/-}$: n=10; Atf3$^{-/-}$: n=7) were allowed to explore freely for 15 min. From days 4 to 8, training sessions were conducted where peanut butter was placed only on predetermined 'correct arms' and mice were allowed to explore. Regular chow was restricted 12 hours before testing. On the testing day, no peanut butter was placed on the arms. A video camera and tracking system (TrackMot) were used to measure the time the mice spent on the predetermined correct arms. The experimental design was shown in FIG. 4E.

Results

FIG. 4 shows the results of the Atf3$^{-/-}$ mice adapting to the hippocampal-dependent Morris water maze (FIGS. 4A-D) and radial arm maze (FIGS. 4E-G). It was observed that the Atf3$^{-/-}$ mice performed normally in the Morris water maze tests, including in visible platform (FIG. 4B), hidden platform (FIG. 4C), and probe trial (FIG. 4D) tests. They also performed normally in the radial arm maze test. No significant difference was recorded for time spent in either the correct arms (FIG. 4F) or the error arms (FIG. 4G). The results of behavioral phenotyping indicated that the Atf3$^{-/-}$ mice specifically exhibited a stronger response to the retrieval of fear memory, whereas their performance in spatial tests was normal.

Example 5: Dendritic Spine Staining Through Golgi-Cox Staining and Density Measurement Because the Atf3$^{-/-}$ mice expressed a PTSD-like, excessive fear response and improved fear memory formation is associated with increase of dendritic spine density (Leonardo Restivo 2009, Shikha Snigdha 2016), whether this behavioral phenotype was correlated with changes in hippocampal spine density was further investigated using the Golgi-Cox staining technique to stain brain sections and measure the density of dendritic spines in the CA1 area of the dorsal hippocampi. The method of dendritic spine staining through Golgi-Cox staining and density measurement is described below.

Gogli-Cox solution was prepared in accordance with the Golgi-Cox Staining Protocol for Neurons and Processes (http://www.ihcworld.com/_protocols/special_stains/golgi_cox.htm). Whole mouse brains were incubated in Golgi-Cox solution for 14 days and in fresh solution for 2 days. After 14 days, the brains were transferred to 30% sucrose and incubated until they sank. 60-am-thick sections of brain were sliced using a vibratome, and placed on slides. The washing procedure of Gibbs et al. was followed. The slides were then covered using a coverslip with permount and left to dry for 24 h. Samples were observed under an optical microscope and the dendritic spine density was calculated using ImageJ. The density of basal dendrites of pyramidal cells in the CA1 region was measured, since polarized growth of apical dendrites is regulated by cell intrinsic programs, while outgrowth of basal dendrites requires extracellular cue(s) sent from the dentate gyrus. For each brain, 20 sections were analyzed, and for each section, 10 neurons (five from the left hippocampus and five from the right hippocampus) were used to calculate the dendritic spine density. "Measure" function of the ImageJ was used to target the longest dendrite under each field with calibrated scale bar, then the number of spines was counted with the function of "Cell count." The dendritic spine density was calculated using the following formula:

Dendritic spine density=Total number of spines/ length of dendrite Results

Figure 5:
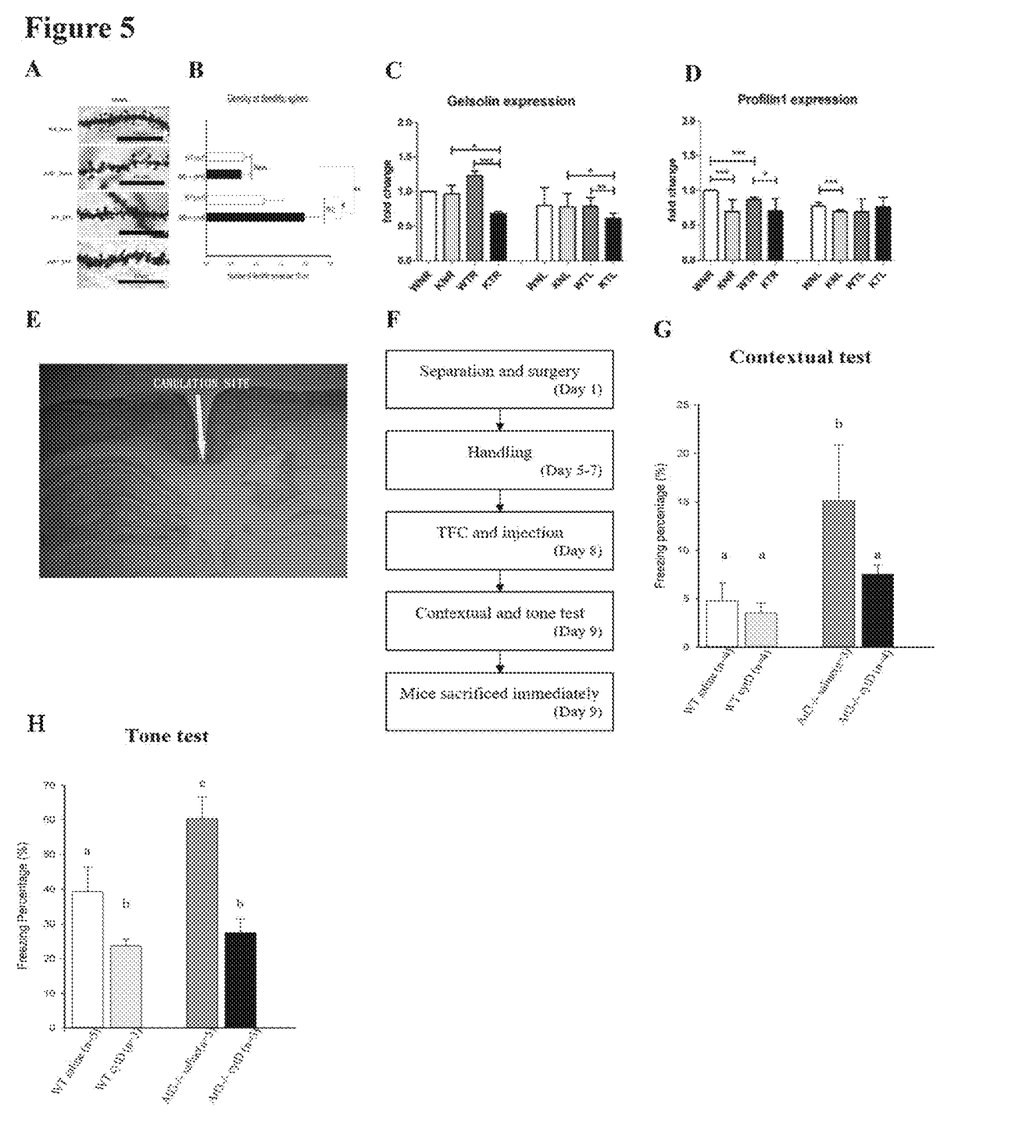

FIG. 5A showed microscopic graphs of dendritic spines in the hippocampal CA1 region. FIG. 5B showed quantification of spine density of basal dendrites measured after retrieval of contextual memory for the Atf3$^{-/-}$ mice and their wild-type littermates with or without trace fear conditioning. As showed in FIGS. 5A and 5B, in correlation with their behavioral performance, the Atf3$^{-/-}$ TFC group had a higher dendritic spine density than did the wild-type TFC and naïve groups.

Example 6: Effect of Actin Depolymerizing Agents on Atf3$^{-/-}$ Mice

Because the Atf3$^{-/-}$ mice exhibited significantly enhanced dendritic spine density in the hippocampal neurons and actin polymerization is the major process involved in dendritic spine formation, whether ATF3 directly regulates the actin polymerization process was investigated by measuring the messenger RNA (mRNA) levels of two major players, Gelsolin and Profilin 1.

Drug Infusion by Stereotactic Injection

At 14 weeks of age, mice (Atf3$^{+/-}$: n=5, Atf3$^{-/-}$: n=9) were anesthetized using a mixture of ketamine, xylazine, and saline (0.55 mL/25 g) in accordance with the regulations of the Lab Animal Center, Tzu Chi University, Taiwan. Mouse heads were restrained in stereotaxic apparatus to ensure movement restriction during surgery. The cannulas were inserted into the third ventricle, just above the hippocampus (anterior-posterior (AP): -2.18 mm from the bregma, dorsoventral (DV): 1.8 mm) as shown in FIG. 5E, and were sealed using acrylic powder. After surgery, the mice were placed in their respective cages to recover for 4 days and were then tested for TFC. Habituation was performed as described in the trace fear conditioning protocol. Using a Hamilton syringe, the actin depolymerizing agent cytochalasin D (Sigma-Aldrich, MO, USA, catalogue No. C8273), dissolved in dimethyl sulfoxide at a concentration of 25 μg/μL, was infused at a rate of 0.5 μL/min for 1 min immediately after fear conditioning on Day 4. Twenty-four hours later, contextual and tone testing was performed as previously described. A few mice were unable to perform the tasks because of loss of mobility after surgery; the data for these mice are not included. Mice were transcardially perfused, and their brains were incubated in Golgi-Cox staining solution. FIG. 5F showed the timeline for intracranial infusion and fear conditioning.

Real-Time Quantitative PCR for Analysis of Gene Expression Levels

After fear conditioning, mice were sacrificed and total RNA was extracted from the hippocampus by using the TRIzol method. Two micrograms of RNA were reverse transcribed using a high-capacity complementary DNA (cDNA) reverse transcription kit (Applied Biosystems, CA, USA). Amplification reactions were performed using the PowerSYBR Green Master Mix (Applied Biosystems) in a Roche 480 Real-Time PCR system (Applied Biosystems StepOne, Applied Biosystems). The relative quantitative threshold cycle (AACt) method was used to analyze the gene expression level. The expression levels of all genes were normalized to the glyceraldehyde 3-phosphate dehydrogenase expression level.

Results

Quantitative reverse transcription polymerase chain reaction (RT-PCR) results indicated that the expression of Gelsolin, the gene encoding a severing protein for actin polymerization, was down-regulated in the bilateral hippocampi of Atf3$^{-/-}$ mice after fear conditioning (FIG. 5C). Since more efficient actin polymerization indicates higher freezing response, this indicated that the normal function of ATF3 is to maintain optimal Gelsolin levels to stop actin polymerization at a certain point and prevent the formation of excess fear response. By contrast, Profilin 1 was significantly down-regulated in the bilateral hippocampi of the naïve ATF3$^{-/-}$ mice and in the right hippocampus of the TFC-trained ATF3$^{-/-}$ mice (FIG. 5D). Since activation of ATF3 is activity dependent, the expression level changes of Profilin 1 occurred mainly in the naïve, not trained, condition, and was not associated with increase of fear responses indicating that Profilin1 expression is not regulated by ATF3.

Further investigation is required to understand how Gelsolin, Profilin 1, and other genes related to actin polymerization are regulated during the formation of fear memory. Cytochalasin D, which inhibits the actin polymerization process in a similar fashion to Gelsolin, was used to confirm a correlation between actin polymerization, dendritic spine density, and fear memory expression. It was determined that the freezing percentages in Atf3$^{-/-}$ mice injected with cytochalasin D were significantly lower compared with the Atf3$^{-/-}$ mice treated with saline and were reduced to a percentage similar to that of wild-type sham control. Corresponding results were determined for both the contextual (FIG. 5G) and tone tests (FIG. 5H).

The results proved that Gelsolin is down-regulated in Atf3$^{-/-}$ mice and enhanced freezing behavior is reversed through actin polymerization inhibition.

Numerous modifications and variations of the invention as set forth in the above illustrative examples are expected to occur to those skilled in the art. Consequently, only such limitations as appear in the appended claims should be placed on the invention.

REFERENCES

1. Ackermann, M. M., A. 6, 1194-1200, doi (2003). (2003). "Activity-induced targeting of profilin and stabilization of dendritic spine morphology." *Nat Neurosci* 6: 1194-1200.
2. Ahlgren, H. e. a. (2014). "The nuclear calcium signaling target, activating transcription factor 3 (ATF3), protects against dendrotoxicity and facilitates the recovery of synaptic transmission after an excitotoxic insult." *The Journal of biological chemistry* 289: 9970-9982.
3. Alvarez, R. P., Biggs, A., Chen, G., Pine, D. S. & Grillon, C. (2008). "The Contextual Fear Conditioning in Humans: Cortical-Hippocampal and Amygdala Contributions." *Journal of neuroscience: the official journal of the Society for Neuroscience* 28: 6211-6219.
4. Brooks, A., Guo Y, Singh M, McCracken J, Xuan Y T, Srivastava S, Bolli R, Bhatnagar A. (2014). "Endoplasmic reticulum stress-dependent activation of ATF3 mediates the late phase of ischemic preconditioning." *J Mol Cell Cardiol* 76: 138-147.
5. Campbell G, H. K., Winterbottom J, Grenningloh G, Lieberman A R, Anderson P N. (2005). "Upregulation of activating transcription factor 3 (ATF3) by intrinsic CNS neurons regenerating axons into peripheral nerve grafts." *Exp Neurol*. 192(5): 340-347.
6. Chen B P, W. C., Hai T (1996). "Analysis of ATF3, a transcription factor induced by physiological stresses and modulated by gadd153/Chop10." *Mol Cell Biol.* 16: 1157-1168.
7. Chun Zhanga, C. G., Junya Kawauchia, Yoshinori Hashimotoa, Nobuo Tsuchidab, Shigetaka Kitajima. (2002). "Transcriptional activation of the human stress-inducible transcriptional repressor ATF3 gene promoter by p53." *Biochemical and Biophysical Research Communications* 297: 1302-1310.
8. Critchley, H. D., Mathias, C. J. & Dolan, R. J. (2002). "Fear Conditioning in Humans: The Influence of Awareness and Autonomic Arousal on Functional Neuroanatomy." *Neuron* 33: 653-663.
9. Francis J S, D. M., During M J (2004). "Over expression of ATF-3 protects rat hippocampal neurons from in vivo injection of kainic acid." *Brain Res Mol Brain Res*. 124: 199-203.
10. Giachero, M., Calfa, G. D. & Molina, V. A. (2013). "Hippocampal structural plasticity accompanies the resulting contextual fear memory following stress and fear conditioning." *Learning &memory* (Cold Spring Harbor, N.Y.) 20: 611-616.
11. Gilchrist, M., W. R. Henderson, Jr., A. E. Clark, R. M. Simmons, X. Ye, K. D. Smith and A. Aderem (2008). "Activating transcription factor 3 is a negative regulator of allergic pulmonary inflammation." *J Exp Med* 205(10): 2349-2357.
12. Goldberg, D. L. M. a. J. L. (2011). "Multiple Transcription Factor Families Regulate Axon Growth and Regenration." *Dev Neurobiol.* 71: 1186-1211.
13. Hai, C. W. A. E. A. G. L. H. V. T. (1997). "ATF3: A transcription repressor involved in stress responses." *FASEB Journal* 11(9).
14. Hai T, H. M. (2001). "The molecular biology and nomenclature of the activating transcription factor/cAMP responsive element binding family of transcription factors: activating transcription factor proteins and homeostasis." *Gene.* 273 (1): 1-11.
15. Hai T, W. C., Marsee D K, Allen A E, Sivaprasad U (1999). "ATF3 and stress responses." *Gene Expr.* 7: 321-335.
16. Hai, T. C., T. (1991). "Cross-family dimerization of transcription factors Fos/Jun and ATF/CREB alters DNA binding specificity." *Proc Natl Acad Sci USA* 88: 3720-3724.
17. Harper, E., Alvares S M, Carter W G. (2005). "Wounding activates p38 map kinase and activation transcription factor 3 in leading keratinocytes." *J Cell Sci* 1(118): 3471-3485.
18. Hartman, M. G. e. a. (2004). "Role for Activating Transcription Factor 3 in Stress-Induced β-Cell Apoptosis." *Molecular and Cellular Biology* 24: 5721-5732.
19. Heinrichs, S. C. e. a. (2013). "Dendritic structural plasticity in the basolateral amygdala after fear conditioning and its extinction in mice." *Behavioural Brain Research.* 248: 80-84.
20. Hlushchenko, I., Koskinen, M. & Hotulainen, P. (2016). "Dendritic spine actin dynamics in neuronal maturation and synaptic plasticity." *Cytoskeleton* (Hoboken. N.J.) 73: 435-441.

21. Hotulainen, P. e. a. (2009). "Defining mechanisms of actin polymerization and depolymerization during dendritic spine morphogenesis." *The Journal of cell biology* 185: 323-339.
22. Hotulainen, P. H., C. C. (2010). "Actin in dendritic spines: connecting dynamics to function." *The Journal of cell biology* 189: 619-629.
23. Hunt D, H.-I. K., Mason M R, Coffin R S, Lieberman A R, Winterbottom J, Anderson P N. (2004). "ATF3 upregulation in glia during Wallerian degeneration: differential expression in peripheral nerves and CNS white matter." *BMC Neurosci.* 5(9).
24. Hunt, D., Raivich, G. & Anderson, P. N. (2012). "Activating transcription factor 3 and the nervous system." *Frontiers in molecular neuroscience* 5(7).
25. Isacsson A, K. M., Dahlin L B (2005). "Induction of activating transcription factor 3 (ATF3) by peripheral nerve compression." *Scand J Plast Reconstr Surg Hand Surg.* 39: 65-72.
26. Izquierdo, I., Furini, C. R. & Myskiw, J. C (2016). "Fear Memory." *Physiological reviews* 96: 695-750.
27. Kehat, I., Hasin, T. & Aronheim, A. (2006). "The role of basic leucine zipper protein-mediated transcription in physiological and pathological myocardial hypertrophy." *Annals of the New York Academy of Sciences* 1080: 97-109.
28. Keifer, O. P., Jr. et al. (2015). "Voxel-based morphometry predicts shifts in dendritic spine density and morphology with auditory fear conditioning." *Nature communications* 6: 7582.
29. Khaitlina, S., Fitz, H. & Hinssen, H. (2013). "The interaction of gelsolin with tropomyosin modulates actin dynamics." *The FEBS journal* 280: 4600-4611.
30. Kim, J., Hwang J Y, Lee D Y, Song E H, Park K J, Kim G H, Jeong E A, Lee Y J, Go M J, Kim D J, Lee S S, Kim B J, Song J, Roh G S, Gao B, Kim W H. (2014). "Chronic ethanol consumption inhibits glucokinase transcriptional activity by Atf3 and triggers metabolic syndrome in vivo." *J Biol Chem* 289(39): 27065-27079.
31. Lamprecht, R., Farb, C. R., Rodrigues, S. M. & LeDoux, J. (2006). "Fear conditioning drives profilin into amygdala dendritic spines." *E. Nat Neurosci* 19: 481-483.
32. Lee, Y. S. e. a. (2013). "Hypothalamic ATF3 is involved in regulating glucose and energy metabolism in mice." *Diabetologia* 56: 1383-1393.
33. Leonardo Restivo, G. V., Bruno Bontempi, and Martine Ammassari-Teule (2009). "The Formation of Recent and Remote Memory Is Associated with Time-Dependent Formation of Dendritic Spines in the Hippocampus and Anterior Cingulate Cortex." *The Journal of Neuroscience* 29(25): 8206-8214.
34. Leuner, B. S., T. (2013). "Stress, anxiety, and dendritic spines: What are the connections?" *J. Neuroscience* 251: 108-119.
35. Li H F, C. C., Liao W J, Lin H, Yang R B. (2010). "ATF3-mediated epigenetic regulation protects against acute kidney injury." *J Am Soc Nephrol.*
36. Lindwall C, D. L., Lundborg G, Kanje M (2004). "Inhibition of c-Jun phosphorylation reduces axonal outgrowth of adult rat nodose ganglia and dorsal root ganglia sensory neurons." *Mol Cell Neurosci.* 27: 267-279.
37. Mantzur, L., Joels, G. & Lamprecht, R. (2009). "Actin polymerization in lateral amygdala is essential for fear memory formation." *Neurobiology of Learning and Memory* 91: 85-88.
38. Maroun, M. e. a. (2013). "Fear extinction deficits following acute stress associate with increased spine density and dendritic retraction in basolateral amygdala neurons." *The European journal of neuroscience* 38: 2611-2620.
39. Matus, A. (2000). "Actin-Based Plasticity in Dendritic Spines." *Science* 290: 754.
40. Middei, S. e. a. (2012). "CREB selectively controls learning-induced structural remodeling of neurons." *Learning & memory* (Cold Spring Harbor. N.Y.) 19.
41. Moczulska, K. E. e. a. (2013). "Dynamics of dendritic spines in the mouse auditory cortex during memory formation and memory recall." *Proceedings of the National Academy of Sciences of the United States of America* 110: 18315-18320.
42. Neuhoff, H. e. a. (2005). "The actin-binding protein profilin I is localized at synaptic sites in an activity-regulated manner." *European Journal of Neuroscience* 21: 15-25.
43. Ni-Chun Chung, Y.-H. H., Chuan-Hsiung Chang, James C. Liao, Chih-Hsien Yang, Chien-Chang Chen, Ingrid Y. Liu (2015). "Behavior Training Reverses Asymmetry in Hippocampal Transcriptome of the Cav3.2 Knockout Mice." *PLoS ONE* 10(3): e0118832.
44. Nie, D. e. a. (2015). "The Stress-Induced Atf3-Gelsolin Cascade Underlies Dendritic Spine Deficits in Neuronal Models of Tuberous Sclerosis Complex." *The Journal of neuroscience: the official journal of the Society for Neuroscience* 35: 10762-10772.
45. Niesmann, K. e. a. (2011). "Dendritic spine formation and synaptic function require neurobeachin." *Nature communications* 2: 557.
46. Nils Z. Borgesius, M. C. d. W., Ingrid van der Pluijm, Azar Omrani, Gerben C. M. Zondag, Gijsbertus T. J. van der Horst, David W. Melton, Jan H. J. Hoeijmakers, Dick Jaarsma, and Ype Elgersma. (2011). "Accelerated Age-Related Cognitive Decline and Neurodegeneration, Caused by Deficient DNA Repair." *The Journal of Neuroscience* 31: 12543-12553.
47. Parsons, R. G. R., K. J. (2013). "Implications of memory modulation for post-traumatic stress and fear disorders." *Nat Neurosci* 16: 146-153.
48. Pernhorst, K., Herms S, Hoffmann P, Cichon S, Schulz H, Sander T, Schoch S, Becker A J, Grote A. (2013). "TLR4, ATF-3 and IL8 inflammation mediator expression correlates with seizure frequency in human epileptic brain tissue." *Seizure* 22(8): 675-678.
49. Rao, J., Qian X, Li G, Pan X, Zhang C, Zhang F, Zhai Y, Wang X, Lu L. Am. (2015). "ATF3-mediated NRF2/HO-1 signaling regulates TLR4 innate immune responses in mouse liver ischemia/reperfusion injury." *J Transplant* 15: 76-87.
50. Sandnes, D., Miiller K M, Akhtar K, Johansen E J, Christoffersen T, Thoresen G H. (2010). "Induction of LRF-1/ATF3 by vasopressin in hepatocytes: role of MAP kinases." *Cell Physiol Biochem* 25(4-5): 523-532.
51. Sargin, D. e. a. (2013). "CREB regulates spine density of lateral amygdala neurons: implications for memory allocation." *Frontiers in behavioral neuroscience* 7(209).
52. Serita, T., Fukushima, H. & Kida, S. (2017). "Constitutive activation of CREB in mice enhances temporal association learning and increases hippocampal CA1 neuronal spine density and complexity." *Scientific reports* 7(42528).
53. Shikha Snigdha, G. A. P., Arpine Petrosyan, XBrad M. Loertscher, Andre' P. Dieskau, XLarry E. Overman, and Carl W. Cotman (2016). "H3K9me3 Inhibition Improves Memory, Promotes Spine Formation, and Increases BDNF Levels in the Aged Hippocampus." *The Journal of Neuroscience* 36(12): 3611-3622.
54. Song, D. Y. e. a. (2008). "Axotomy-induced dopaminergic neurodegeneration is accompanied with c-Jun phosphorylation and activation transcription factor 3 expression." *Experimental neurology* 209: 268-278.
55. St Germain C, N. N., Ma L, Garbuio K, Hai T, Dimitroulakos (2010). "Cisplatin induces cytotoxicity through the mitogen-activated protein kinase pathways and activating transcription factor 3." *J. Neoplasia* 12: 527-538.
56. Takeda M, K. H., Takamiya A, Yoshida A, Kiyama H (2000). "Targeted Injury-specific expression of activating transcription factor-3 in retinal ganglion cells and its colocalized expression with phosphorylated c-Jun." *Invest Ophthalmol Vis Sci* 41: 2412-2421.
57. Taketani, K. e. a. (2012). "Key role of ATF3 in p53-dependent DR5 induction upon DNA damage of human colon cancer cells." *Oncogene* 31: 2210-2221.
58. Takumi Yoshida, H. S., Michihiro Mitobe, Ken Tsuchiya, Satsuki Shirota, Sayoko Nishimura, Shunji Shiohira, Hiroshi Ito, Kiyoshi Nobori, Steven R. Gullans, Takashi Akiba and Kosaku Nitta (2008). "ATF3 Protects against Renal Ischemia-Reperfusion Injury." *JASN* 19(2): 217-224.
59. Tanaka, Y. e. a. (2011). "Systems analysis of ATF3 in stress response and cancer reveals opposing effects on pro-apoptotic genes in p53 pathway." *Plos one* 6: e26848.
60. Tsujino H, K. E., Fukuoka T, Dai Y, Tokunaga A, Miki K, Yonenobu K, Ochi T, Noguchi K (2000). "Activating transcription factor 3 (ATF3) induction by axotomy in sensory and motoneurons: A novel neuronal marker of nerve injury." *Mol Cell Neurosci.* 15: 170-182.
61. Tsujino H, K. E., Fukuoka T, Dai Y, Tokunaga A, Miki K, Yonenobu K, Ochi T, Noguchi K (2000). "Activating transcription factor 3 (ATF3) induction by axotomy in sensory and motoneurons: A novel neuronal marker of nerve injury." *Mol Cell Neurosci.* 15(2): 170-182.
62. Wang, L. e. a. (2012). "Increased inflammation and brain injury after transient focal cerebral ischemia in activating transcription factor 3 knockout mice." *Neuroscience* 220: 100-108.
63. Wu Z Y, W. Z., Sun S J, Yuan J, Jiao S C. (2014). "Activating transcription factor 3 promotes colon cancer metastasis." *Tumour Biol* 35(8): 8329-8334.
64. Yin, X., Dewille, J. W. & Hai, T. (2008). "A potential dichotomous role of ATF3, an adaptive-response gene, in cancer development." *Oncogene* 27: 2118-2127.
65. Yuan, X. e. a. (2013). "ATF3 suppresses metastasis of bladder cancer by regulating gelsolin-mediated remodeling of the actin cytoskeleton." *Cancer research* 73: 3625-3627.
66. Zhang S J, B. B., Lau D, Hayer S, Dick O, Schwaninger M, Veltkamp R, Zou M, Weiss U, Bading H. (2011). "A signaling cascade of nuclear calcium-CREB-ATF3 activated by synaptic NMDA receptors defines a gene repression module that protects against extrasynaptic NMDA receptor-induced neuronal cell death and ischemic brain damage." *J Neurosci* 31(13): 4978-4990.
67. Trendowski, M. (2015). "Using Cytochalasins to Improve Current Chemotherapeutic Approaches" *Anticancer Agents Med Chem* 15(3): 327-335.

What is claimed is:

1. A method for reducing excess fear response in a subject in which the expression of normal ATF3 is reduced or absent, comprising
administering to the subject a therapeutically effective amount of cytochalasin D.

2. The method of claim 1, wherein the excess fear response is post-traumatic stress disorder (PTSD).

3. The method of claim 1, wherein the therapeutically effective amount of cytochalasin D is selected from the ranges of from about 0.01 mg/kg to about 20 mg/kg, from about 0.05 mg/kg to about 15 mg/kg, from about 0.1 mg/kg to about 10 mg/kg, and from about 0.5 mg/kg to about 5 mg/kg.

4. The method of claim 1, further comprising administering another anti-anxiety drug.

5. The method of claim 4, wherein the anti-anxiety drug is selected from alprazolam, clonazepam, chlordiazepoxide, diazepam, lorazepam and oxazepam.

6. The method of claim 1, wherein the method is for use in combination with psychotherapy.

7. The method of claim 1, wherein the subject does not express ATF3.

\* \* \* \* \*

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1
agagcttcag caatggtttg c                                                 21

<210> SEQ ID NO 2
<211> LENGTH: 22
<212> TYPE: DNA
<213> ORGANISM: Artificial Sequence
<220> FEATURE:
<223> OTHER INFORMATION: Synthetic Primer

<400> SEQUENCE: 2
tgaagaaggt aaacacaccg tg                                                22

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
atcagcagcc tctgttccac                                                   20
```